US005989818A

United States Patent [19]

Labrie et al.

[11] Patent Number: 5,989,818

[45] Date of Patent: Nov. 23, 1999

[54] DNA ENCODING HUMAN RSEC6 RELATED PROTEIN

[75] Inventors: Samuel T. Labrie, Mountain View; David G. Streeter, Boulder Creek, both of Calif.

[73] Assignee: Incyte Pharmaceuticals, Inc., Palo Alto, Calif.

[21] Appl. No.: 08/941,262

[22] Filed: Sep. 30, 1997

[51] Int. Cl.$^{6}$ .............................. C12Q 1/68; C12P 21/06; C12N 15/00; C07H 21/04

[52] U.S. Cl. ............................ 435/6; 435/69.1; 435/70.1; 435/71.1; 435/71.2; 435/252.3; 435/254.11; 435/320.1; 435/325; 536/23.5; 935/4; 935/6; 935/22; 935/66

[58] Field of Search .................................. 536/23.1, 23.6, 536/23.4, 23.5; 435/6, 69.1, 69.3, 69.7, 70.1, 71.1, 71.2, 325, 252.3, 254.11, 320.1; 935/4, 6, 22, 66

[56] References Cited

PUBLICATIONS

Mahbubani etal, Chapter 31 in "PCR Technology Current Innovations" Griffin etal eds, CRC Press Inc, 1994.

Rothman, J.E. and Wieland, F.T. "Protein Sorting by Transport Vesicles" *Science* (1996) 272:227–234.

Tellman, J.T. et al., "Molecular Identification of Two Novel Munc–18 Isoforms Expressed in Non–neuronal Tissues" *J.Biol.Chem.* (1995) 270:5857–5863.

Hata, Y. and Sudhof, T.C. "A Novel Ubiquitous Form of Munc–18 Interacts with Multiple Syntaxins" *J.Biol.Chem.* (1995) 270:13022–13028.

Ting, et al., "rSec6 and rSec8, mammalian homologs of yeast proteins essential for secretion" *Proc.Natl.Adac. Sci.USA* (1995) 92:9613–9617.

Hsu, S. et al., "The Mammalian Brain rsec6/8 Complex" *Neuron* (1996) 17:1209–1219.

Bunk, Steve "Scientists, Clinicians Optimistic About New Antischizophrenia Drugs" *The Scientist* (1997) 11:1,5.

Ting, A.E. et al., (GI 1163173), GenBank Sequence Database (Accession U32575), National Center for Biotechnology Information, National Library of Medicine, Bethesda, Maryland, 20894.

Karayiorgou, M. et al., "Schizophrenia susceptibility associated with interstitial deletions of chromosome 22q11" *Proc.Natl.Acad.Sci.USA* (1995) 92:7612–7616.

Lachman, H.M. et al., "Linkage Studies Suggest a Possible Locus for Bipolar Disorder Near the Velo–Cardio–Facial Syndrome Region on Chromosome 22" *Amer.J.Med.Gene.* (1997) 74:121–128.

Hudson, T.J. et al., "An STS–Based Map of the Human Genome." *Science* (1995) 270:1945–1954.

*Primary Examiner*—Patricia A. Duffy
*Attorney, Agent, or Firm*—Incyte Pharmaceuticals, Inc.

[57] ABSTRACT

The invention provides a human rSec6 related vesicle transport protein (HSEC6) and polynucleotides which identify and encode HSEC6. The invention also provides expression vectors, host cells, agonists, antibodies and antagonists. The invention also provides methods for treating disorders associated with expression of HSEC6.

10 Claims, 12 Drawing Sheets

```
                9                  18                   27                   36                   45                  54
5' NAG GAG GTG CAC AGA GAA CAC CCC TAG CAT GAA CAG TGT GAG GAT TCC ACC AGC
                                                   C   E   D   S   T   S

               63                  72                   81                   90                   99                 108
   TTT TTC ACC ATG AAG GAG ACA GAC CGG GAG GCC GTT GCG ACA GCA GTG CAA AGG
   F   F   T   M   K   E   T   D   R   E   A   V   A   T   A   V   Q   R

              117                 126                  135                  144                  153                 162
   GTT GCT GGG ATG CTC CAG CGC CCG GAC CAG CTG GAC AAG GTG GAG CAG TAT CGC
   V   A   G   M   L   Q   R   P   D   Q   L   D   K   V   E   Q   Y   R

              171                 180                  189                  198                  207                 216
   AGG AGA GAA GCG CGG AAG AAG GCC TCC GTG GAG GCC AGA TTG AAG GCC GCC ATC
   R   R   E   A   R   K   K   A   S   V   E   A   R   L   K   A   A   I

              225                 234                  243                  252                  261                 270
   CAG TCA CAG TTG GAC GGG GTG CGC ACA GGC CTC AGC CAG CTC CAC AAC GCC CTG
   Q   S   Q   L   D   G   V   R   T   G   L   S   Q   L   H   N   A   L

              279                 288                  297                  306                  315                 324
   AAT GAC GTC AAA GAC ATC CAG CAG TCG CTG GCA GAC GTC AGC AAG GAC TGG AGG
   N   D   V   K   D   I   Q   Q   S   L   A   D   V   S   K   D   W   R

              333                 342                  351                  360                  369                 378
   CAG AGC ATC AAC ACC ATT GAG AGC CTC AAG GAC GTC AAA GAC GCC GTG GTG CAG
   Q   S   I   N   T   I   E   S   L   K   D   V   K   D   A   V   V   Q
```

FIGURE1A

```
            387         396         405         414         423         432
CAC AGC CAG CTC GCC GCA GCC GTG GAG AAC CTC AAG AAC ATC TTC TCA GTG CCT
H   S   Q   L   A   A   A   V   E   N   L   K   N   I   F   S   V   P

            441         450         459         468         477         486
GAG ATT GTG AGG GAG ACC CAG GAC CTA ATT GAA CAA GGG GCA CTC CTG CAA GCC
E   I   V   R   E   T   Q   D   L   I   E   Q   G   A   L   L   Q   A

            495         504         513         522         531         540
CAC CGG AAG CTG ATG GAC CTG GAG TGC TCC CGG GAC GGG CTG ATG TAC GAG CAG
H   R   K   L   M   D   L   E   C   S   R   D   G   L   M   Y   E   Q

            549         558         567         576         585         594
TAC CGC ATG GAC AGT GGG AAC ACG CGT GAC ATG ACC CTC ATC CAT GGC TAC TTT
Y   R   M   D   S   G   N   T   R   D   M   T   L   I   H   G   Y   F

            603         612         621         630         639         648
GGC AGC ACG CAG GGG CTC TCT GAT GAG CTG GCT AAG CAG CTG TGG ATG GTG CTG
G   S   T   Q   G   L   S   D   E   L   A   K   Q   L   W   M   V   L

            657         666         675         684         693         702
CAG AGG TCA CTG GTC ACT GTC CGC CGT GAC CCC ACC TTG CTG GTC TCA GTT GTC
Q   R   S   L   V   T   V   R   R   D   P   T   L   L   V   S   V   V

            711         720         729         738         747         756
AGG ATC ATT GAA AGG GAA GAG AAA ATT GAC AGG CGC ATA CTT GAC CGG AAA AAG
R   I   I   E   R   E   E   K   I   D   R   R   I   L   D   R   K   K
```

FIGURE1B

```
        765         774         783         792         801         810
CAA ACT GGC TTT GTT CCT CCT GGG AGG CCC AAG AAT TGG AAG GAG AAA ATG TTC
Q   T   G   F   V   P   P   G   R   P   K   N   W   K   E   K   M   F

        819         828         837         846         855         864
ACC ATC TTG GAG AGG ACT GTG ACC ACC AGA ATT GAG GGC ACA CAG GCA GAT ACC
T   I   L   E   R   T   V   T   T   R   I   E   G   T   Q   A   D   T

        873         882         891         900         909         918
AGA GAG TCT GAC AAG ATG TGG CTT GTC CGC CAC CTG GAA ATT ATA AGG AAG TAC
R   E   S   D   K   M   W   L   V   R   H   L   E   I   I   R   K   Y

        927         936         945         954         963         972
GTC CTG GAT GAC CTC ATT GTC GCC AAA AAC CTG ATG GTT CAG TGC TTT CCT CCC
V   L   D   D   L   I   V   A   K   N   L   M   V   Q   C   F   P   P

        981         990         999        1008        1017        1026
CAC TAT GAG ATC TTT AAG AAC CTC CTG AAC ATG TAC CAC CAA GCC CTG AGC ACG
H   Y   E   I   F   K   N   L   L   N   M   Y   H   Q   A   L   S   T

       1035        1044        1053        1062        1071        1080
CGG ATG CAG GAC CTC GCA TCG GAA GAC CTG GAA GCC AAT GAG ATC GTG AGC CTC
R   M   Q   D   L   A   S   E   D   L   E   A   N   E   I   V   S   L

       1089        1098        1107        1116        1125        1134
TTG ACG TGG GTC TTA AAC ACC TAC ACA AGT ACT GAG ATG ATG AGG AAC GTG GAG
L   T   W   V   L   N   T   Y   T   S   T   E   M   M   R   N   V   E
```

FIGURE1C

```
        1143        1152        1161        1170        1179        1188
CTG GCC CCG GAA GTG GAT GTC GGC ACC CTG GAG CCA TTG CTT TCT CCA CAC GTG
L   A   P   E   V   D   V   G   T   L   E   P   L   L   S   P   H   V

        1197        1206        1215        1224        1233        1242
GTC TCT GAG CTG CTT GAC ACG TAC ATG TCC ACG CTC ACT TCA AAC ATC ATC GCC
V   S   E   L   L   D   T   Y   M   S   T   L   T   S   N   I   I   A

        1251        1260        1269        1278        1287        1296
TGG CTG CGG AAA GCG CTG GAG ACA GAC AAG AAA GAC TGG GTC AAA GAG ACA GAG
W   L   R   K   A   L   E   T   D   K   K   D   W   V   K   E   T   E

        1305        1314        1323        1332        1341        1350
CCA GAA GCC GAC CAG GAC GGG TAC TAC CAG ACC ACA CTC CCT GCC ATT GTC TTC
P   E   A   D   Q   D   G   Y   Y   Q   T   T   L   P   A   I   V   F

        1359        1368        1377        1386        1395        1404
CAG ATG TTT GAA CAG AAT CTT CAA GTT GCT GCT CAG ATA AGT GAA GAT TTG AAA
Q   M   F   E   Q   N   L   Q   V   A   A   Q   I   S   E   D   L   K

        1413        1422        1431        1440        1449        1458
ACA AAG GTA CTA GTT TTA TGT CTT CAG CAG ATG AAT TCT TTC CTA AGC AGA TAT
T   K   V   L   V   L   C   L   Q   Q   M   N   S   F   L   S   R   Y

        1467        1476        1485        1494        1503        1512
AAA GAT GAA GCG CAC TGG TAT AAA GAA GAG CAC CTG AGG AAT CGG CAG CAC CCT
K   D   E   A   H   W   Y   K   E   E   H   L   R   N   R   Q   H   P
```

FIGURE1D

```
        1521        1530        1539        1548        1557        1566
CAC TGC TAC GTT CAG TAC ATG ATC GCC ATC ATC AAC AAC TGC CAG ACC TTC AAG
H   C   Y   V   Q   Y   M   I   A   I   I   N   N   C   Q   T   F   K

        1575        1584        1593        1602        1611        1620
GAA TCC ATA GTC AGT TTA AAA AGA AAG TAT TTA AAG AAT GAA GTG GAA GAG GGT
E   S   I   V   S   L   K   R   K   Y   L   K   N   E   V   E   E   G

        1629        1638        1647        1656        1665        1674
GTG TCT CCG AGC CAG CCC AGC ATG GAC GGG ATT TTA GAC GCC ATC GCG AAG GAG
V   S   P   S   Q   P   S   M   D   G   I   L   D   A   I   A   K   E

        1683        1692        1701        1710        1719        1728
GGC TGC AGC GGT TTG CTG GAG GAG GTC TTC CTG GAC CTG GAG CAA CAT CTG AAT
G   C   S   G   L   L   E   E   V   F   L   D   L   E   Q   H   L   N

        1737        1746        1755        1764        1773        1782
GAA TTG ATG ACG AAG AAG TGG CTA TTA GGG TCA AAC GCT GTA GAC ATT ATC TGT
E   L   M   T   K   K   W   L   L   G   S   N   A   V   D   I   I   C

        1791        1800        1809        1818        1827        1836
GTC ACC GTG GAA GAC TAT TTC AAC GAT TTT GCC AAA ATT AAA AAG CCG TAT AAG
V   T   V   E   D   Y   F   N   D   F   A   K   I   K   K   P   Y   K

        1845        1854        1863        1872        1881        1890
AAG AGG ATG ACG GCC GAG GCG CAC CGG CGC GTG GTG GTG GAG TAC CTG CGG GCG
K   R   M   T   A   E   A   H   R   R   V   V   V   E   Y   L   R   A
```

FIGURE1E

```
              1899           1908           1917           1926           1935           1944
GTC ATG CAG AAG CGC ATT TCC TTC CGG AGC CCG GAG GAG CGC AAG GAG GGT GCC
V   M   Q   K   R   I   S   F   R   S   P   E   E   R   K   E   G   A

              1953           1962           1971           1980           1989           1998
GAG AAG ATG GTT AGG GAG GCA GAG CAG CTG CGC TTC CTG TTC CGG AAG CTG GCG
E   K   M   V   R   E   A   E   Q   L   R   F   L   F   R   K   L   A

              2007           2016           2025           2034           2043           2052
TCC GGT TTC GGG GAA GAC GTG GAC GGA TAC TGC GAC ACC ATC GTG GCT GTG GCC
S   G   F   G   E   D   V   D   G   Y   C   D   T   I   V   A   V   A

              2061           2070           2079           2088           2097           2106
GAA GTG ATC AAG CTG ACA GAC CCT TCT CTG CTC TAC CTG GAG GTC TCC ACT CTG
E   V   I   K   L   T   D   P   S   L   L   Y   L   E   V   S   T   L

              2115           2124           2133           2142           2151           2160
GTC AGC AAG TAT CCA GAC ATC AGG GAT GAC CAC ATC GGT GCG CTG CTG GCT GTG
V   S   K   Y   P   D   I   R   D   D   H   I   G   A   L   L   A   V

              2169           2178           2187           2196           2205           2214
CGT GGG GAC GCC AGC CGT GAC ATG AAG CAG ACC ATC ATG GAG ACC CTG GAG CAG
R   G   D   A   S   R   D   M   K   Q   T   I   M   E   T   L   E   Q
```

FIGURE 1F

```
        2223        2232        2241        2250        2259        2268
GGC CCA GCA CAG GCC AGC CCC AGC TAC GTG CCC CTC TTC AAG GAC ATT GTG GTG
G   P   A   Q   A   S   P   S   Y   V   P   L   F   K   D   I   V   V

        2277        2286        2295        2304        2313        2322
CCC AGC CTG AAC GTG GCC AAG CTG CTC AAG TAG CCT CCG CCG GCC TGC CCT GCT
P   S   L   N   V   A   K   L   L   K

        2331        2340        2349        2358        2367        2376
CGC CCC TCC ACA GCC TCG GTC CCT GCC TTT AGA AAC GCG GGA CAG CTG ATT GCT

        2385        2394        2403        2412        2421        2430
CTC CTT GGC CAC ACG TGC TCC TTT TAG CTG CAC GGC CTG TCT TTA GGT GCC AGT

        2439        2448        2457
GTG ATG CAC CGG STG TGG TCG AGT GAG CGT CCC GA 3'
```

FIGURE 1G

```
1    -CEDSTSFFTMKETDREAVATAVQRVAGMLQRPDQLDKVE  1874686
1    MCKDSACFSTMKETDLEAVATAVQRVAGMLQRPDQLDKVE  g1163174

40   QYRRREARKKASVEARLKAAIQSQLDGVRTGLSQLHNALN  1874686
41   QYRRREARKKASVEARLKAAIQSQLDGVRTGLSQLHNALN  g1163174

80   DVKDIQQSLADVSKDWRQSINTIESLKDVKDAVVQHSQLA  1874686
81   DVKDIQQSLADVSKDWRQSINTIESLKDVKDAVVQHSQLA  g1163174

120  AAVENLKNIFSVPEIVRETQDLIEQGALLQAHRKLMDLEC  1874686
121  AAVENLKNIFSVPEIVRETQDLIEQGALLQAHRKLMDLEC  g1163174

160  SRDGLMYEQYRMDSGNTRDMTLIHGYFGSTQGLSDELAKQ  1874686
161  SRDGLMCEQYRMDSGNKRDMTLIHGYFGSTQGLSDELAKQ  g1163174

200  LWMVLQRSLVTVRRDPTLLVSVVRIIEREEKIDRRILDRK  1874686
201  LWMVLQRSLVTVRRDPTLLVSVVRIIEREEKIDRRILDRK  g1163174

240  KQTGFVPPGRPKNWKEKMFTILERTVTTRIEGTQADTRES  1874686
241  KQTGFVPPGRPKNWKEKMFAVLDRTVTTRIEGTQADTRES  g1163174
```

FIGURE 2A

```
280 DKMWLVRHLEIIRKYVLDDLIVAKNLMVQCFPPHYEIFKN 1874686
281 DKMWLVRHLEIIRKYVLDDLVIAKNLLVQCFPPHYDIFKN g1163174

320 LLNMYHQALSTRMQDLASEDLEANEIVSLLTWVLNTYTST 1874686
321 LLSMYHQALSIRMQDLASEDLEANEIVSLLTWVLNTYTSA g1163174

360 EMMRNVELAPEVDVGTLEPLLSPHVVSELLDTYMSTLTSN 1874686
361 EMMGNVELAPEVDVNALEPLLSPNVVSELLDTYMSTLTSN g1163174

400 IIAWLRKALETDKKDWVKETEPEADQDGYYQTTLPAIVFQ 1874686
401 IIAWLRKALETDKKDWSKETEPEADQDGYYQTTLPAIVFQ g1163174

440 MFEQNLQVAAQISEDLKTKVLVLCLQQMNSFLSRYKDEAH 1874686
441 MFEQNLQVAAQISEDLKTKVLVLCLQQMNSFLSRYKEEAQ g1163174

480 WYKEEHLRNRQHPHCYVQYMIAIINNCQTFKESIVSLKRK 1874686
481 LYKEEHLRNRQHPHCYVQYMVAIINNCQTFKESIISLKRK g1163174

520 YLKNEVEEGVSPSQPSMDGILDAIAKEGCSGLLEEVFLDL 1874686
521 YLKPETEESLCQSQPSMDGILDAIAKEGCSSLLEEVFLDL g1163174
```

FIGURE 2B

```
560 EQHLNELMTKKWLLGSNAVDIICVTVEDYFNDFAKIKKPY 1874686
561 EQHLNELMTKKWMLGSNAVDIICVTVEDYFNDFAKIKKPY g1163174

600 KKRMTAEAHRRVVVEYLRAVMQKRISFRSPEERKEGAEKM 1874686
601 KKRMTAEAHRRVVVEYLRAVMQKRISFRSAEERKEGAEKM g1163174

640 VREAEQLRFLFRKLASGFGEDVDGYCDTIVAVAEVIKLTD 1874686
641 VREAEQLRFLFRKLASGFGEDADGHCDTIVAVAEVIKLTD g1163174

680 PSLLYLEVSTLVSKYPDIRDDHIGALLAVRGDASRDMKQT 1874686
681 PSLLYLEVSTLVSKYPDIRDDHIGALLALRGDASRDMKQT g1163174

720 IMETLEQGPAQASPSYVPLFKDIVVPSLNVAKLLK 1874686
721 IMETLEQGPMQASPNYVPIFQEIVVPSLNVAKLLK g1163174
```

FIGURE 2C

DNA ENCODING HUMAN RSEC6 RELATED PROTEIN

FIELD OF THE INVENTION

This invention relates to nucleic acid and amino acid sequences of a human rSec6 (rat secretory pathway protein 6) related vesicle transport protein and to the use of these sequences in the diagnosis, prevention, and treatment of cancer, immune disorders, and neurodegenerative disorders.

BACKGROUND OF THE INVENTION

Vesicle transport is the general process in eukaryotic cells by which proteins synthesized in the endoplasmic reticulum (ER) are transported via the Golgi network to the various compartments in the cell where they will function. Other proteins are transported to the cell surface by this process where they may be secreted (exocytosis). Such proteins include membrane bound receptors or other membrane proteins, neurotransmitters, hormones, and digestive enzymes. The transport process uses a series of transport vesicles that shuttle a protein from one membrane-bound compartment (donor compartment) to another (acceptor compartment) until the protein reaches its proper destination (Rothman, J. E and Wieland, F. T. (1996) Science 727:227–34).

The process begins with the budding of a vesicle out of the donor membrane. The vesicle contains the protein to be transported and is surrounded by a protective coat made up of protein subunits recruited from the cytosol. The initial budding process and coating processes are controlled by a cytosolic GTP-binding protein, either SAR or ARF. When GTP binds and activates SAR, it binds to the donor membrane and initiates the vesicle assembly process. The coated vesicle containing the GTP-SAR complex detaches from the donor compartment and is transported through the cytosol. During the transport process, the SAR-bound GTP is hydrolyzed to GDP, and the inactivated SAR dissociates from the transport vesicle. At this point, the protective coat becomes unstable and dissociates from the enclosed vesicle. The uncoated vesicle is recognized by its acceptor compartment through exposed surface identifiers (v-SNAREs) which bind with corresponding molecules on the acceptor compartment membrane (t-SNAREs). The transport process ends when the vesicle fuses with the target membrane.

The fusion of the transport vesicle with the acceptor compartment membrane, that follows the initial binding of the two compartments, involves the formation of a complex between the v-SNARE, t-SNARE, and certain other proteins recruited from the cytosol. Many of these other proteins have been identified although their exact functions in the fusion complex remain uncertain (Tellam, J. T. et al. (1995) J. Biol. Chem. 270:5857–63; Hata, Y. and Sudhof, T. C. (1995) J. Biol. Chem. 270:13022–28). N-ethylmaleimide sensitive factor (NSF) and soluble NSF-attachment protein (SNAP) are two such proteins that are conserved from yeast to human and function in most intracellular membrane fusion reactions.

Neurotransmission in mammals involves a specialized form of vesicle transport which uses a signaling molecule (neurotransmitter) stored in a membrane-bound vesicle (synaptic vesicle) at the terminus of a nerve cell. A change in electrical potential at the nerve terminal results from excitation of the nerve and triggers the release of the neurotransmitter from the synaptic vesicles by exocytosis. The neurotransmitter rapidly diffuses across the junction (synaptic cleft) separating the first (presynaptic) nerve cell from the second (postsynaptic) and provokes a change in electrical potential in the latter by binding to and opening transmitter-gated ion channels located in the plasma membrane of the postsynaptic cell. In this manner, the neural signal is transmitted from one nerve cell to the other.

Many of the proteins involved in synaptic vesicle transport have been identified and the biochemical interactions between them have been characterized. Interestingly, many of these proteins are homologous to yeast proteins involved in yeast secretory pathways (sec). For example, yeast Sec4 is a GTPase essential for late stages of vesicle secretion and is homologous to mammalian Rab3a GTPase. Yeast Sec6p and Sec8p are components of a 19.5S particle that interact with Sec4. Mammalian counterparts to these two proteins, rSec6 and rSec8, have been identified from rat brain cDNA libraries (Ting, A. E. et al. (1995) Proc. Natl. Acad. Sci. 92:9613–17). rSec6 is an 87 kDa protein with 22% amino acid identity to Sec6, and rSec8 is a 110 kDa protein with 20% identity to Sec8. Further studies revealed that rSec6 and rSec8 are components of a 17S complex in rat brain that is composed of 8 proteins with a combined molecular weight of 743 kDa (Hsu, S-C et al. (1996) Neuron 17:1209–19). The rSec6/rSec8 complex coimmunoprecipitates with syntaxin, a plasma membrane t-SNARE protein involved in neurotransmission. This indicates a role for the rSec6/rSec8 complex in the neurotransmission process. rSec6 and rSec8 are similarly expressed in all regions of rat brain, suggesting that both proteins are required by all brain cells (Hsu et al. supra). In addition, both proteins are found in a variety of non-neuronal tissues including lung, muscle, ovary, and kidney, indicating that they may function in a variety of secretory pathways in addition to neurotransmission (Ting et al. supra; Hsu et al. supra).

Few structural motifs have been identified that characterize these vesicle transport proteins. However, both rSec6 and rSec8 contain a region near their N-terminus capable of forming coiled-coil domains, a motif frequently observed in vesicle trafficking proteins and believed to be important for interactions with other proteins (Ting et al. supra). rSec8 also contains a leucine-rich domain near its N-terminus that is postulated to interact with GTP-binding proteins such as Rab3a.

The control of vesicle transport processes, particularly the process of neurotransmission, has important implications for the control of various diseases and disorders. Current drug treatments for the brain disorder schizophrenia target receptors for various neurotransmitters such as dopamine and serotonin (Bunk, S. (1997) The Scientist 11:1–5). However these treatments have numerous unwanted side effects.

The discovery of a new human rSec6 related protein and the polynucleotides encoding it satisfies a need in the art by providing new compositions which are useful in the diagnosis, prevention and treatment of cancer, immune disorders, and neurodegenerative disorders.

SUMMARY OF THE INVENTION

The invention features a substantially purified polypeptide, human rSec6 related vesicle transport protein (HSEC6), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding HSEC6 under conditions suitable for the expression of the polypeptide; and b) recovering the polypeptide from the host cell culture.

The invention also provides a pharmaceutical composition comprising a substantially purified HSEC6 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a neurodegenerative disorder comprising administering to a subject in need of such treatment an effective amount of a pharmaceutical composition comprising purified HSEC6.

The invention also provides a method for treating or preventing cancer comprising administering to a subject in need of such treatment an effective amount of a purified antagonist of HSEC6.

The invention also provides a method for treating or preventing an immune disorder comprising administering to a subject in need of such treatment an effective amount of a purified antagonist of HSEC6.

The invention also provides a method for detecting a polynucleotide which encodes HSEC6 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding HSEC6 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of HSEC6. The alignment was produced using MACDNASIS PRO software (Hitachi Software Engineering Co. Ltd. San Bruno, Calif.).

FIGS. 2A, 2B, and 2C show the amino acid sequence alignments between HSEC6 (1874686; SEQ ID NO:1) and rat rSec6 protein (GI 1163174; SEQ ID NO:3), produced using the multisequence alignment program of LASERGENE software (DNASTAR Inc, Madison Wis.).

DESCRIPTION OF THE INVENTION

Figure 3A:
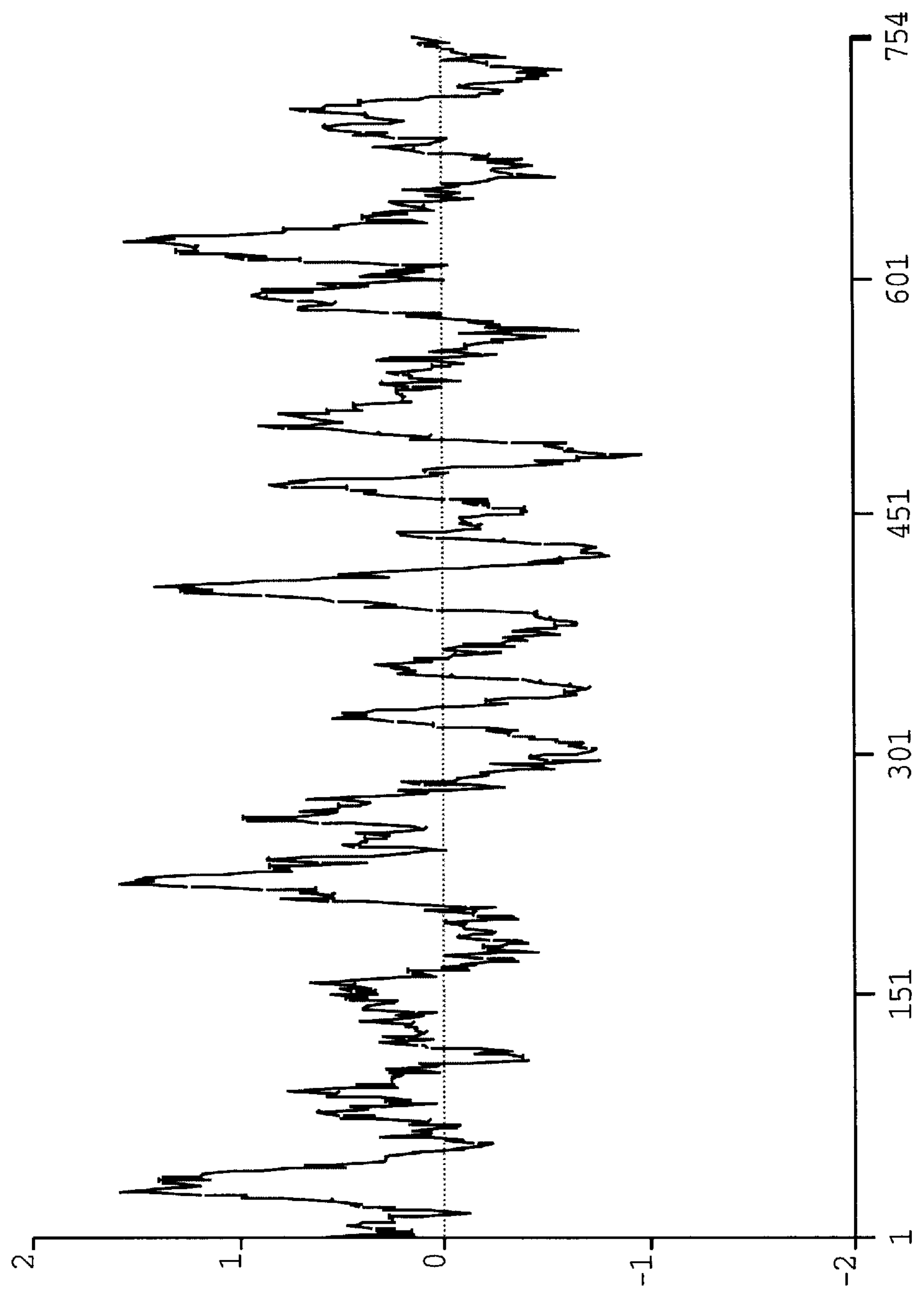
FIGS. 3A and 3B show the hydrophobicity plots for HSEC6 (SEQ ID NO:1) and rat rSec6 (SEQ ID NO:3), respectively; the positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

HSEC6, as used herein, refers to the amino acid sequences of substantially purified HSEC6 obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HSEC6, increases or prolongs the duration of the effect of HSEC6. Agonists may include proteins, nucleic acids, carbohydrates, or any other molecules which bind to and modulate the effect of HSEC6.

An "allele" or "allelic sequence", as used herein, is an alternative form of the gene encoding HSEC6. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HSEC6 as used herein include those with deletions, insertions, or substitutions of different nucleotides resulting in a polynucleotide that encodes the same or a functionally equivalent HSEC6. Included within this definition are polymorphisms which may or may not be readily detectable using a particular probe of the polynucleotide encoding HSEC6, and improper or unexpected hybridization to alleles with a locus other than the normal chromosomal locus for the polynucleotide sequence encoding HSEC6. The encoded protein may also be "altered" and contain deletions, insertions, or substitutions of amino acid residues which produce a silent change and result in a functionally equivalent HSEC6. Deliberate amino acid substitutions may be made on the basis of similarity in polarity, charge, solubility, hydrophobicity, hydrophilicity, and/or the amphipathic nature of the residues as long as the biological or immunological activity of HSEC6 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of HSEC6 are preferably about 5 to about 15 amino acids in length and retain the biological activity or the immunological activity of HSEC6. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to HSEC6, decreases the amount or the duration of the effect of the biological or immunological activity of HSEC6. Antagonists may include proteins, nucleic acids, carbohydrates, antibodies or any other molecules which decrease the effect of HSEC6.

As used herein, the term "antibody" refers to intact molecules as well as fragments thereof, such as Fa, $F(ab')_2$, and Fv, which are capable of binding the epitopic determinant. Antibodies that bind HSEC6 polypeptides can be prepared using intact polypeptides or fragments containing small peptides of interest as the immunizing antigen. The polypeptide or oligopeptide used to immunize an animal can be derived from the translation of RNA, or synthesized chemically, and conjugated to a carrier protein, if desired. Commonly used carriers that are chemically coupled to peptides include bovine serum albumin, thyroglobulin, and keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HSEC6, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding HSEC6 (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR Kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding HSEC6 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid, encoding or complementary strand. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization, and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 1K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides on a substrate, such as paper, nylon or other type of membrane, filter, chip, glass slide, or any other suitable solid support.

The term "modulate", as used herein, refers to a change in the activity of HSEC6. For example, modulation may cause an increase or a decrease in protein activity, binding characteristics, or any other biological, functional or immunological properties of HSEC6.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay or on a microarray. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length HSEC6 and fragments thereof.

The term "sample", as used herein, is used in its broadest sense. A biological sample suspected of containing nucleic acid encoding HSEC6, or fragments thereof, or HSEC6 itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HSEC6, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The Invention

The invention is based on the discovery of a new human rSec6 related vesicle transport protein (hereinafter referred to as "HSEC6"), the polynucleotides encoding HSEC6, and the use of these compositions for the diagnosis, prevention, or treatment of cancer, immune disorders, and neurodegenerative disorders.

Nucleic acids encoding the HSEC6 of the present invention were first identified in Incyte Clone 1874686 from the leukocyte cell cDNA library (LEUKNOT02) using a computer search for amino acid sequence alignments. A consensus sequence, SEQ ID NO:2, was derived from the following overlapping and/or extended nucleic acid sequences: Incyte Clones 828214 (PROSNOT06), 1309124 (COLNFET02), 1671186 (BMARNOT03), 1676290 (BLADNOT05), 1874686 (LEUKNOT02), 2075231 (ISLTNOT01), 2643215 (LUNGTUT08), 2695875 (UTRSNOT12), 3029646 (HEARFET02), and 3178893 (TLYJNOT01).

Figure 3B:
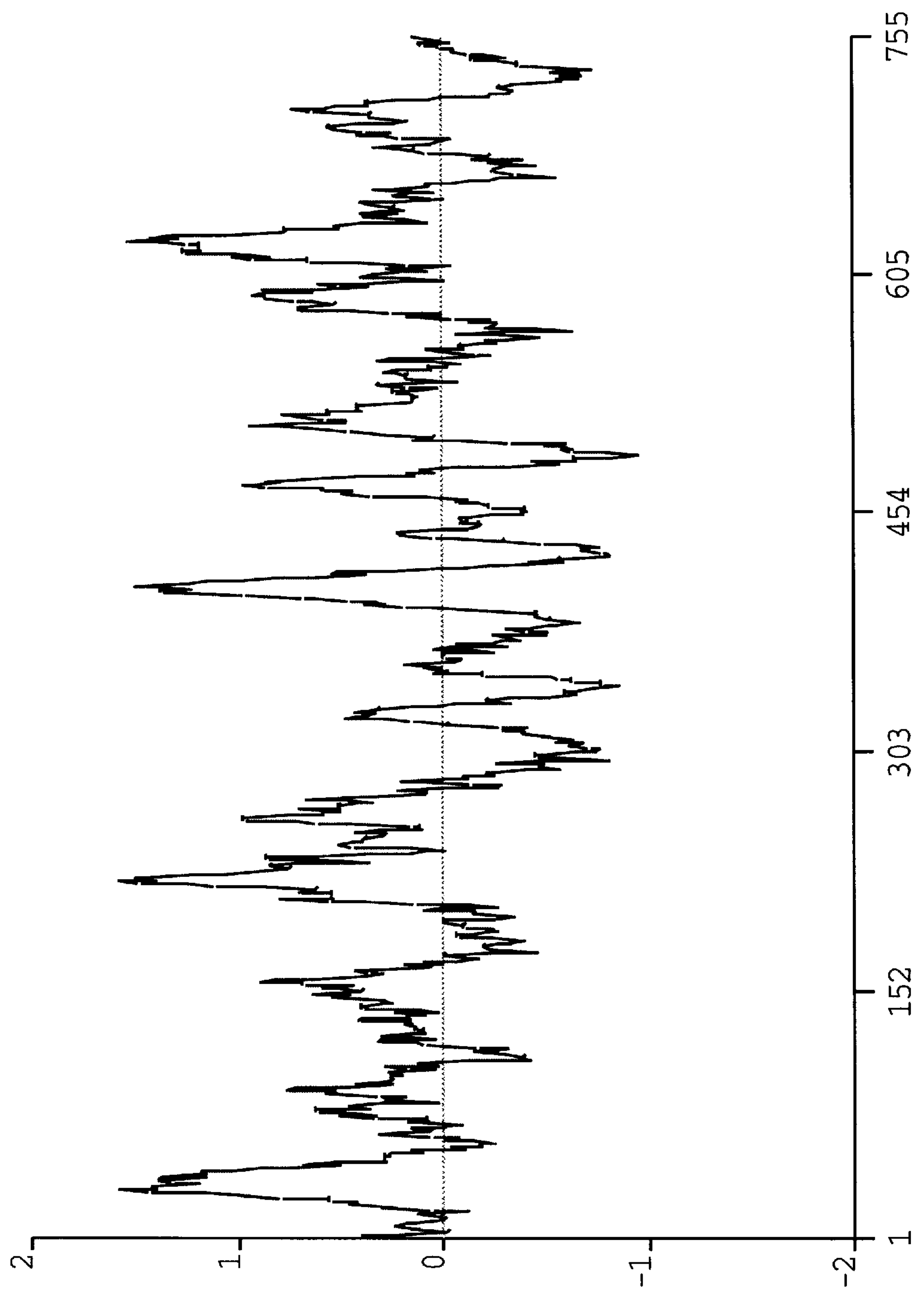

In one embodiment, the invention encompasses a polypeptide comprising the amino acid sequence of SEQ ID NO:1, as shown in FIGS. 1A, 1B, 1C, 1D, 1E, 1F, and 1G. HSEC6 is 754 amino acids in length and has numerous potential protein kinase phosphorylation sites. Potential cAMP-dependent protein kinase (PKA) phosphorylation sites are found at $S_{51}$, $T_{242}$, $T_{604}$, and $S_{625}$. Fifteen potential casein kinase II phosphorylation sites are spread throughout the molecule, including $T_{13}$, $T_{267}$, and $T_{719}$. Thirteen potential protein kinase C (PKC) phosphorylation sites are also found, including $S_{104}$, $T_{410}$, and S625. A single potential tyrosine kinase phosphorylation site is found at $Y_{481}$. A potential RGD cell receptor attachment site is found at $R_{709}$, and a potential glycosaminoglycan attachment site is found in the sequence $S_{655}$GFG. As shown in FIGS. 2A and 2B, HSEC6 has chemical and structural homology with the rat rSec6 (GI 1163174; SEQ ID NO:3). In particular, HSEC6 and rSec6 share 94% identity. HSEC6 and rSec6 share 97% identity in the region of amino acids 97 to 171 where the coiled-coil domain has been identified in rSec6. Most of the various potential protein kinase phosphorylation sites found in HSEC6 are found in rSec6, as well as the potential RGD cell attachment site and the glycosaminoglycan attachment site. As illustrated by FIGS. 3A and 3B, HSEC6 and rSec6 have rather similar hydrophobicity plots. HSEC6 has been mapped to chromosome 22ql11. Northern analysis shows the expression of this sequence in various libraries, at least 41% of which are immortalized or cancerous, at least 22% of which involve inflammation and the immune response, and at least 24% of which involve the brain or neural tissue.

The invention also encompasses HSEC6 variants. A preferred HSEC6 variant is one having at least 80%, and more preferably at least 90%, amino acid sequence identity to the HSEC6 amino acid sequence (SEQ ID NO:1) and which retains at least one biological, immunological or other functional characteristic or activity of HSEC6. A most preferred HSEC6 variant is one having at least 95% amino acid sequence identity to SEQ ID NO:1.

The invention also encompasses polynucleotides which encode HSEC6. Accordingly, any nucleic acid sequence which encodes the amino acid sequence of HSEC6 can be used to produce recombinant molecules which express HSEC6. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of nucleotide sequences encoding HSEC6, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSEC6, and all such variations are to be considered as being specifically disclosed.

Although nucleotide sequences which encode HSEC6 and its variants are preferably capable of hybridizing to the nucleotide sequence of the naturally occurring HSEC6 under appropriately selected conditions of stringency, it may be advantageous to produce nucleotide sequences encoding HSEC6 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSEC6 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HSEC6 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HSEC6 or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq DNA polymerase (Perkin Elmer), thermostable T7 polymerase (Amersham Pharmacia Biotech, Piscataway, N.J.), or combinations of polymerases and proofreading exonucleases such as those found in the ELONGASE Amplification System marketed by Life Technologies (Gaithersburg, Md.). Preferably, the process is automated with machines such as the Micro Lab 2200 (Hamilton, Reno, Nev.), DNA ENGINE Thermal Cycler (PTC200; MJ Research, Watertown, Mass.) and the ABI Catalyst and 373 and 377 DNA Sequencers (Perkin Elmer).

The nucleic acid sequences encoding HSEC6 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSEC6 may be used in recombinant DNA molecules to direct expression of HSEC6, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HSEC6.

As will be understood by those of skill in the art, it may be advantageous to produce HSEC6-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HSEC6 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HSEC6 may be ligated to a heterologous sequence to encode a fusion protein. For example, to screen peptide libraries for inhibitors of HSEC6 activity, it may be useful to encode a chimeric HSEC6 protein that can be recognized by a commercially available antibody. A fusion protein may also be engineered to contain a cleavage site located between the HSEC6 encoding sequence and the heterologous protein sequence, so that HSEC6 may be cleaved and purified away from the heterologous moiety.

In another embodiment, sequences encoding HSEC6 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HSEC6, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of HSEC6, or any part thereof, may be altered during direct synthesis and/or combined using chemical methods with sequences from other proteins, or any part thereof, to produce a variant polypeptide.

In order to express a biologically active HSEC6, the nucleotide sequences encoding HSEC6 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HSEC6 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HSEC6. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector-enhancers, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HSEC6, vectors based on SV40 or EBV may be used with an appropriate selectable marker.

In bacterial systems, a number of expression vectors may be selected depending upon the use intended for HSEC6. For example, when large quantities of HSEC6 are needed for the induction of antibodies, vectors which direct high level expression of fusion proteins that are readily purified may be used. Such vectors include, but are not limited to, the multifunctional *E. coli* cloning and expression vectors such as BLUESCRIPT phagemid (Stratagene), in which the sequence encoding HSEC6 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HSEC6 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HSEC6. For example, in one such system, *Autographa californica* nuclear polyhedrosis virus (AcNPV) is used as a vector to express foreign genes in *Spodoptera frugiperda* cells or in Trichoplusia larvae. The sequences encoding HSEC6 may be cloned into a non-essential region of the virus, such as the polyhedrin gene, and placed under control of the polyhedrin promoter. Successful insertion of HSEC6 will render the polyhedrin gene inactive and produce recombinant virus lacking coat protein. The recombinant viruses may then be used to infect, for example, *S. frugiperda* cells or Trichoplusia larvae in which HSEC6 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HSEC6 may be ligated into an adenovirus transcription/translation complex consisting of the late promoter and tripartite leader sequence. Insertion in a non-essential E1 or E3 region of the viral genome may be used to obtain a viable virus which is capable of expressing HSEC6 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HSEC6. Such signals include the ATG initiation codon and adjacent sequences. In cases where sequences encoding HSEC6, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC) Bethesda, Md.) and may be chosen to ensure the correct modification and processing of the foreign protein.

For long-term, high-yield production of recombinant proteins, stable expression is preferred. For example, cell lines which stably express HSEC6 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HSEC6 is inserted within a marker gene sequence, transformed cells containing sequences encoding HSEC6 can be identified by the absence of marker gene function. Alternatively, a marker gene can be placed in tandem with a sequence encoding HSEC6 under the control of a single promoter. Expression of the marker gene in response to induction or selection usually indicates expression of the tandem gene as well.

Alternatively, host cells which contain the nucleic acid sequence encoding HSEC6 and express HSEC6 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HSEC6 can be detected by DNA-DNA or DNA-RNA hybridization or amplification using probes or fragments or fragments of polynucleotides encoding HSEC6. Nucleic acid amplification based assays involve the use of oligonucleotides or oligomers based on the sequences encoding HSEC6 to detect transformants containing DNA or RNA encoding HSEC6.

A variety of protocols for detecting and measuring the expression of HSEC6, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSEC6 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSEC6 include oligolabeling, nick translation, end-labeling or PCR amplification using a labeled nucleotide. Alternatively, the sequences encoding HSEC6, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Amersham Pharmacia & Biotech, Promega and U.S. Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HSEC6 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HSEC6 may be designed to contain signal sequences which direct secretion of HSEC6 through a prokaryotic or eukaryotic cell membrane. Other constructions may be used to join sequences encoding HSEC6 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSEC6 may be used to facilitate purification. One such expression vector provides for expression of a fusion protein containing HSEC6 and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying HSEC6 from the fusion protein. A discussion of vectors which contain fusion proteins is provided in Kroll, D. J. et al. (1993; DNA Cell Biol. 12:441–453).

In addition to recombinant production, fragments of HSEC6 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of HSEC6 may be chemically synthesized separately and combined using chemical methods to produce the full length molecule.

THERAPEUTICS

Chemical and structural homology exists between HSEC6 and rSec6 from rat (GI1163174). In addition, HSEC6 is expressed in cancer and immortalized cell lines, tissues associated with inflammation and the immune response, and in brain and neural tissues. Therefore, HSEC6 appears to play a role in cancer, immune disorders, and neurodegenerative disorders. In particular, increased expression or activity of HSEC6 appears to be associated with cancer and immune disorders, while decreased expression or activity appears to be associated with neurodegenerative disorders. The ability to control neurotransmitter release by controlling the expression or activity of HSEC6 provides a more beneficial therapeutic approach to the treatment of neurodegenerative disorders such as schizophrenia than current treatments (Bunk, supra). Genetic expression of HSEC6 has been mapped to the chromosome 22q11 locus, where chromosomal defects and deletions have been associated with development of neurodegenerative disorders such as schizophrenia, velo-cardial facial syndrome, and bipolar disorder (manic depressive illness) (Karayiorgou, M. et al. (1995) Proc. Natl. Acad. Sci. 92:7612–16; Lachman, H. M. et al. (1997) Am. J. Med. Genet. 74:121–28).

Therefore, in one embodiment, HSEC6 or a fragment or derivative thereof may be administered to a subject to prevent or treat a neurodegenerative disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, velo-cardial facial syndrome, bipolar disorder and Tourette's disorder.

In another embodiment, a pharmaceutical composition comprising purified HSEC6 may be administered to a subject to prevent or treat a neurodegenerative disorder including, but not limited to, those described above.

In another embodiment, a vector capable of expressing HSEC6, or a fragment or a derivative thereof, may also be administered to a subject to prevent or treat a neurodegenerative disorder including, but not limited to, those described above.

In still another embodiment, an agonist which modulates the activity of HSEC6 may also be administered to a subject to prevent or treat a neurodegenerative disorder including, but not limited to, those described above.

In another embodiment, an antagonist of HSEC6 may be administered to a subject to prevent or treat cancer. Types of cancer may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus In one aspect, an antibody which specifically binds HSEC6 may be used directly as an antagonist or indirectly as a targeting or delivery mechanism for bringing a pharmaceutical agent to cells or tissue which express HSEC6.

In another embodiment, an antagonist of HSEC6 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves'disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding HSEC6 may be administered to a subject to treat or prevent a cancer including, but not limited to, those described above.

In another embodiment, a vector expressing the complement of the polynucleotide encoding HSEC6 may be administered to a subject to treat or prevent an immune disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSEC6 may be produced using methods which are generally known in the art. In particular, purified HSEC6 may be used to produce antibodies or to screen libraries of pharmaceutical agents to identify those which specifically bind HSEC6.

Antibodies to HSEC6 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSEC6 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSEC6 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HSEC6 amino acids may be fused with those of another protein such as keyhole limpet hemocyanin and antibody produced against the chimeric molecule.

Monoclonal antibodies to HSEC6 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 5 312:604–608; Takeda, S. et al. (1985) Nature 314:452–454). Alternatively, techniques described for the production of single chain antibodies may be adapted, using methods known in the art, to produce HSEC6-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 10 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833 3837; Winter, G. et al. (1991) Nature 349:293–299).

Antibody fragments which contain specific binding sites for HSEC6 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSEC6 and its specific antibody. A two-site, monoclonal-based immunoassay utilizing monoclonal antibodies reactive to two non-interfering HSEC6 epitopes is preferred, but a competitive binding assay may also be employed (Maddox, supra).

In another embodiment of the invention, the polynucleotides encoding HSEC6, or any fragment or complement thereof, may be used for therapeutic purposes. In one aspect, the complement of the polynucleotide encoding HSEC6 may be used in situations in which it would be desirable to block the transcription of the mRNA. In particular, cells may be transformed with sequences complementary to polynucleotides encoding HSEC6. Thus, complementary molecules or fragments may be used to modulate HSEC6 activity, or to achieve regulation of gene function. Such technology is now well known in the art, and sense or antisense oligonucleotides or larger fragments, can be designed from various locations along the coding or control regions of sequences encoding HSEC6.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HSEC6. These techniques are described both in Sambrook et al. (supra) and in Ausubel et al. (supra).

Genes encoding HSEC6 can be turned off by transforming a cell or tissue with expression vectors which express high levels of a polynucleotide or fragment thereof which encodes HSEC6. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HSEC6 (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSEC6.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSEC6. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSEC6, antibodies to HSEC6, mimetics, agonists, antagonists, or inhibitors of HSEC6. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSEC6, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSEC6 or fragments thereof, antibodies of HSEC6, agonists, antagonists or inhibitors of HSEC6, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HSEC6 may be used for the diagnosis of conditions or diseases characterized by expression of HSEC6, or in assays to monitor patients being treated with HSEC6, agonists, antagonists or inhibitors. The antibodies useful for diagnostic purposes may be prepared in the same manner as those described above for therapeutics. Diagnostic assays for HSEC6 include methods which utilize the antibody and a label to detect HSEC6 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSEC6 are known in the art and provide a basis for diagnosing altered or abnormal levels of HSEC6 expression. Normal or standard values for HSEC6 expression are established by combining body fluids or cell extracts taken from normal mammalian subjects, preferably human, with antibody to HSEC6 under conditions suitable for complex formation. The amount of standard complex formation may be quantified by various methods, but preferably by photometric, means. Quantities of HSEC6 expressed in subject, control and disease, samples from biopsied tissues are compared with the standard values. Deviation between standard and subject values establishes the parameters for diagnosing disease.

In another embodiment of the invention, the polynucleotides encoding HSEC6 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSEC6 may be correlated with disease. The diagnostic assay may be used to distinguish between absence, presence, and excess expression of HSEC6, and to monitor regulation of HSEC6 levels during therapeutic intervention.

In one aspect, hybridization with PCR probes which are capable of detecting polynucleotide sequences, including genomic sequences, encoding HSEC6 or closely related molecules, may be used to identify nucleic acid sequences which encode HSEC6. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSEC6, alleles, or related sequences.

Probes may also be used for the detection of related sequences, and should preferably contain at least 50% of the nucleotides from any of the HSEC6 encoding sequences. The hybridization probes of the subject invention may be DNA or RNA and derived from the nucleotide sequence of SEQ ID NO:2 or from genomic sequence including promoter, enhancer elements, and introns of the naturally occurring HSEC6.

Means for producing specific hybridization probes for DNAs encoding HSEC6 include the cloning of nucleic acid sequences encoding HSEC6 or HSEC6 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSEC6 may be used for the diagnosis of conditions or disorders which are associated with expression of HSEC6. Examples of such conditions or disorders include neurodegenerative disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, velo-cardial facial syndrome, bipolar disorder and Tourette's disorder; cancers such as adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. The polynucleotide sequences encoding HSEC6 may be used in Southern or northern analysis, dot blot, or other membrane-based technologies; in PCR technologies; or in dipstick, pin, ELISA assays or microarrays utilizing fluids or tissues from patient biopsies to detect altered HSEC6 expression. Such qualitative or quantitative methods are well known in the art.

In a particular aspect, the nucleotide sequences encoding HSEC6 may be useful in assays that detect activation or induction of various cancers, particularly those mentioned above. The nucleotide sequences encoding HSEC6 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HSEC6 in the sample indicates the presence of the associated disease.

Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSEC6, a normal or standard profile for expression is established. This may be accomplished by combining body fluids or cell extracts taken from normal subjects, either animal or human, with a sequence, or a fragment thereof, which encodes HSEC6, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSEC6 may involve the use of PCR. Such oligomers may be chemically synthesized, generated enzymatically, or produced in vitro. Oligomers will preferably consist of two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSEC6 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HSEC6 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HSEC6 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSEC6, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSEC6 and the agent being tested, may be measured.

Another technique for drug screening which may be used provides for high throughput screening of compounds having suitable binding affinity to the protein of interest as described in published PCT application WO84/03564. In this method, as applied to HSEC6 large numbers of different small test compounds are synthesized on a solid substrate, such as plastic pins or some other surface. The test compounds are reacted with HSEC6, or fragments thereof, and washed. Bound HSEC6 is then detected by methods well known in the art. Purified HSEC6 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSEC6 specifically compete with a test compound for binding HSEC6. In this manner, the antibodies can be used to detect the presence of any peptide which shares one or more antigenic determinants with HSEC6.

In additional embodiments, the nucleotide sequences which encode HSEC6 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I LEUKNOT02 cDNA Library Construction

The LEUKNOT02 cDNA library was constructed from whole white blood cells obtained from a healthy 45-year-old female donor of blood type O+ and who tested positive for CMV.

Whole white blood cells were isolated from one unit of buffy coat using gradient density centrifugation over a double gradient of HISTOPAQUE (Sigma Aldrich, St. Louis, Mo.). Cells of the granulocyte series were pooled with the peripheral blood mononuclear cells. The harvested cells were lysed using a Polytron homogenizer (PT-3000; (Brinkmann Instruments, Westbury, N.J.) in guanidinium isothiocyanate solution. Both lysates were centrifuged over a 5.7 M CsCl cushion using an SW28 rotor in a Beckman L8-70M Ultracentrifuge (Beckman Instruments, Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNAse at 37° C. RNA extraction and precipitation were repeated as before. The mRNA was then isolated using the OLIGOTEX kit (QIAGEN, Inc., Chatsworth, Calif.) and used to construct the cDNA libraries.

The mRNA was handled according to the recommended protocols in the SUPERSCRIPT Plasmid System for cDNA Synthesis and Plasmid Cloning (Cat. #18248-013, Life Technologies). cDNAs were fractionated on a SEPHAROSE CL4B column (Cat. #275105-01 Amersham Pharmacia Biotech), and those cDNAs exceeding 400 bp were ligated into (Incyte Pharmeceuticals, Palo Alto, Calif.) The plasmid pINCY was subsequently transformed into DH5a competent cells (Cat. #18258-012, Life Technologies).

II Isolation and Sequencing of cDNA Clones

Plasmid DNA was released from the cells and purified using the REAL Prep 96 Plasmid Kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared and then sequenced by the method of Sanger et al. (1975, J. Mol. Biol. 94:441f), using a Micro Lab 2200 (Hamilton) in combination with DNA ENGINE thermal cycler (MJ Research) and Applied Biosystems 377 DNA Sequencing systems (Perkin-Elmer); and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-4}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul (1993) supra; Altshul (1990) supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\ \text{sequence identity} \times \%\ \text{maximum}\,BLAST\ \text{score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSEC6 occurs. Abundance and percent abundance are also reported. Abundance directly reflects the number of times a particular transcript is represented in a cDNA library, and percent abundance is abundance divided by the total number of sequences examined in the cDNA library.

V Extension of HSEC6 Encoding Polynucleotides

The nucleic acid sequence of the Incyte Clone 1874686 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Life Technologies) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the DNA ENGINE thermal cycler (M.J. Research) and the following parameters:

Step 1 94° C. for 1 min (initial denaturation)

Step 2 65° C. for 1 min

Step 3 68° C. for 6 min

Step 4 94° C. for 15 sec

Step 5 65° C. for 1 min

Step 6 68° C. for 7 min

Step 7 Repeat step 4–6 for 15 additional cycles

Step 8 94° C. for 15 sec

Step 9 65° C. for 1 min

Step 10 68° C. for 7:15 min

Step 11 Repeat step 8–10 for 12 cycles

Step 12 72° C. for 8 min

Step 13 4° C. (and holding)

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using the QiaQuick kit (Qiagen), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec

Step 2 94° C. for 20 sec

Step 3 94° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [$\gamma$-$^{32}$P] adenosine triphosphate (Amersham Pharmacia Biotech) and T4 polynucleotide kinase (DuPont NEN, Boston, Mass.). The labeled oligonucleotides are substantially purified with SEPHADEX G-25 superfine resin column (Amersham Pharmacia Biotech). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots in a Phosphoimager cassette (Amersham Pharmacia Biotech), for several hours, hybridization patterns are compared.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HSEC6-encoding sequence, or any part thereof, is used to decrease or inhibit expression of naturally occurring HSEC6. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HSEC6, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSEC6-encoding transcript.

IX Expression of HSEC6

Expression of HSEC6 is accomplished by subcloning the cDNAs into appropriate vectors and transforming the vectors into host cells. In this case, the cloning vector is also used to express HSEC6 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HSEC6 into the bacterial growth media which can be used directly in the following assay for activity.

X Demonstration of HSEC6 Activity

HSEC6 activity may be determined by the binding of reconstituted HSEC6/rSec8 complex with the synaptic vesicle protein Rab3a. This is based on the known binding of yeast Sec6/8 complex with the GTPase, Sec4p and the analogous binding of rSec6/8 complex with Rab3a GTPase (Ting, et al. supra; Hsu et al. supra). HSEC6 is radiolabeled with $^{35}$S and reconstituted into the HSEC6/rSec8 743 kDa complex as defined by Hsu et al. (supra) replacing the rSec6 component. An Rab3a binding substrate is prepared in the form of a glutathione S-transferase (GST)-Rab3a fusion protein. For each assay, approximately 2 μg of GST-Rab3a fusion protein absorbed to glutathione-agarose beads is incubated with varying amounts of $^{35}$S-labeled HSEC6 complex in a suitable buffer for 3 hours at 4° C. The agarose beads are separated from the incubation by sedimentation and washed several times to remove unbound protein. HSEC6 and other bound proteins are solubilized from the agarose beads by boiling in wash buffer and separated by SDS-polyacrylamide gel electrophoresis. HSEC6 is visualized by autoradiography. The amount of radioactivity recovered is proportional to the activity of HSEC6 in the assay.

XI Production of HSEC6 Specific Antibodies

HSEC6 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A (Perkin-Elmer) using Fmoc-chemistry, and coupled to keyhole limpet hemocyanin (KLH, Sigma Aldrich) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HSEC6 Using Specific Antibodies

Naturally occurring or recombinant HSEC6 is substantially purified by immunoaffinity chromatography using antibodies specific for HSEC6. An immunoaffinity column is constructed by covalently coupling HSEC6 antibody to an activated chromatographic resin, such as CNBr-activated SEPHAROSE (Amersham Pharmacia Biotech). After the coupling, the resin is blocked and washed according to the manufacturer's instructions.

Media containing HSEC6 is passed over the immunoaffinity column, and the column is washed under conditions that allow the preferential absorbance of HSEC6 (e.g., high ionic strength buffers in the presence of detergent). The column is eluted under conditions that disrupt antibody/HSEC6 binding (eg, a buffer of pH 2–3 or a high concentration of a chaotrope, such as urea or thiocyanate ion), and HSEC6 is collected.

XIII Identification of Molecules Which Interact with HSEC6

HSEC6 or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled HSEC6, washed and any wells with labeled HSEC6 complex are assayed. Data obtained using different concentrations of HSEC6 are used to calculate values for the number, affinity, and association of HSEC6 with the candidate molecules.

XIV Mapping of the Gene Which Encodes HSEC6

HSEC6 was mapped to 22ql11 by hybridizing it to an arrayed BAC library containing 27,600 clones using the LIFESEQ ATLAS database (Incyte Pharmaceuticals). HSEC6 hybridized to BAC 662-F-09. The microsatellite marker D22S539, which also hybridizes to 662-F-09, has been mapped on the MIT radiation hybrid map and the Généthon genetic map to 22q11 (Hudson, T. J. et al. (1995) Science 270:1945–54). Therefore HSEC6 is also mapped to 22q11.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the human rSec6 related vesicle transport protein having the amino acid sequence consisting of SEQ ID NO:1.

2. An isolated polynucleotide sequence which is complementary to the polynucleotide sequence of claim 1.

3. An isolated and purified polynucleotide sequence comprising SEQ ID NO:2.

4. An isolated polynucleotide sequence which is completely complementary to the polynucleotide sequence of claim 3.

5. An expression vector containing the polynucleotide sequence of claim 1.

6. A host cell containing the vector of claim 5.

7. A method for producing a polypeptide comprising the amino acid sequence of SEQ ID NO:1, the method comprising the steps of:

a) culturing the host cell of claim 6 under conditions suitable for the expression of the polypeptide; and b) recovering the polypeptide from the host cell culture.

8. A method for detecting a polynucleotide which encodes human rSec6 related vesicle transport protein in a biological sample comprising the steps of:

a) hybridizing the polynucleotide of claim 2 to nucleic acid material of a biological sample, thereby forming a hybridization complex;

b) washing the sample under high stringency conditions; and c) detecting said hybridization complex, wherein the presence of said complex correlates with the presence of a polynucleotide encoding human rSec6 related vesicle transport protein in said biological sample.

9. The method of claim 8 wherein the nucleic acid material is amplified by the polymerase chain reaction prior to hybridization.

10. A method of using a polynucleotide to screen a library of molecules or compounds to identify at least one molecule or compound which specifically binds the polynucleotide, the method comprising:

a) combining the polynucleotide of claim 3 with a library of molecules under conditions to allow specific binding, and b) detecting specific binding, thereby identifying a molecule or compound which specifically binds the nucleic acid molecule.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 754 amino acids
(B) TYPE: amino acid
(C) STRANDEDNESS: single
(D) TOPOLOGY: linear (vii) IMMEDIATE SOURCE:
(A) LIBRARY: LEUKNOT02
(B) CLONE: 1874686

(xi) SEQUENCE DESCRIPTION: SEQ ID NO:1:

```
Cys Glu Asp Ser Thr Ser Phe Phe Thr Met Lys Glu Thr Asp Arg Glu
 1               5                  10                  15

Ala Val Ala Thr Ala Val Gln Arg Val Ala Gly Met Leu Gln Arg Pro
            20                  25                  30

Asp Gln Leu Asp Lys Val Glu Gln Tyr Arg Arg Arg Glu Ala Arg Lys
        35                  40                  45

Lys Ala Ser Val Glu Ala Arg Leu Lys Ala Ala Ile Gln Ser Gln Leu
    50                  55                  60

Asp Gly Val Arg Thr Gly Leu Ser Gln Leu His Asn Ala Leu Asn Asp
65                  70                  75                  80

Val Lys Asp Ile Gln Gln Ser Leu Ala Asp Val Ser Lys Asp Trp Arg
                85                  90                  95

Gln Ser Ile Asn Thr Ile Glu Ser Leu Lys Asp Val Lys Asp Ala Val
            100                 105                 110

Val Gln His Ser Gln Leu Ala Ala Ala Val Glu Asn Leu Lys Asn Ile
        115                 120                 125

Phe Ser Val Pro Glu Ile Val Arg Glu Thr Gln Asp Leu Ile Glu Gln
    130                 135                 140

Gly Ala Leu Leu Gln Ala His Arg Lys Leu Met Asp Leu Glu Cys Ser
145                 150                 155                 160

Arg Asp Gly Leu Met Tyr Glu Gln Tyr Arg Met Asp Ser Gly Asn Thr
                165                 170                 175

Arg Asp Met Thr Leu Ile His Gly Tyr Phe Gly Ser Thr Gln Gly Leu
            180                 185                 190

Ser Asp Glu Leu Ala Lys Gln Leu Trp Met Val Leu Gln Arg Ser Leu
        195                 200                 205

Val Thr Val Arg Arg Asp Pro Thr Leu Leu Val Ser Val Val Arg Ile
    210                 215                 220

Ile Glu Arg Glu Glu Lys Ile Asp Arg Arg Ile Leu Asp Arg Lys Lys
225                 230                 235                 240

Gln Thr Gly Phe Val Pro Pro Gly Arg Pro Lys Asn Trp Lys Glu Lys
                245                 250                 255

Met Phe Thr Ile Leu Glu Arg Thr Val Thr Thr Arg Ile Glu Gly Thr
            260                 265                 270

Gln Ala Asp Thr Arg Glu Ser Asp Lys Met Trp Leu Val Arg His Leu
        275                 280                 285

Glu Ile Ile Arg Lys Tyr Val Leu Asp Asp Leu Ile Val Ala Lys Asn
    290                 295                 300

Leu Met Val Gln Cys Phe Pro Pro His Tyr Glu Ile Phe Lys Asn Leu
```

-continued

```
305                 310                 315                 320

Leu Asn Met Tyr His Gln Ala Leu Ser Thr Arg Met Gln Asp Leu Ala
                325                 330                 335

Ser Glu Asp Leu Glu Ala Asn Glu Ile Val Ser Leu Leu Thr Trp Val
            340                 345                 350

Leu Asn Thr Tyr Thr Ser Thr Glu Met Met Arg Asn Val Glu Leu Ala
        355                 360                 365

Pro Glu Val Asp Val Gly Thr Leu Glu Pro Leu Leu Ser Pro His Val
    370                 375                 380

Val Ser Glu Leu Leu Asp Thr Tyr Met Ser Thr Leu Thr Ser Asn Ile
385                 390                 395                 400

Ile Ala Trp Leu Arg Lys Ala Leu Glu Thr Asp Lys Lys Asp Trp Val
                405                 410                 415

Lys Glu Thr Glu Pro Glu Ala Asp Gln Asp Gly Tyr Tyr Gln Thr Thr
            420                 425                 430

Leu Pro Ala Ile Val Phe Gln Met Phe Glu Gln Asn Leu Gln Val Ala
        435                 440                 445

Ala Gln Ile Ser Glu Asp Leu Lys Thr Lys Val Leu Val Leu Cys Leu
    450                 455                 460

Gln Gln Met Asn Ser Phe Leu Ser Arg Tyr Lys Asp Glu Ala His Trp
465                 470                 475                 480

Tyr Lys Glu Glu His Leu Arg Asn Arg Gln His Pro His Cys Tyr Val
                485                 490                 495

Gln Tyr Met Ile Ala Ile Ile Asn Asn Cys Gln Thr Phe Lys Glu Ser
            500                 505                 510

Ile Val Ser Leu Lys Arg Lys Tyr Leu Lys Asn Glu Val Glu Glu Gly
        515                 520                 525

Val Ser Pro Ser Gln Pro Ser Met Asp Gly Ile Leu Asp Ala Ile Ala
    530                 535                 540

Lys Glu Gly Cys Ser Gly Leu Leu Glu Glu Val Phe Leu Asp Leu Glu
545                 550                 555                 560

Gln His Leu Asn Glu Leu Met Thr Lys Lys Trp Leu Leu Gly Ser Asn
                565                 570                 575

Ala Val Asp Ile Ile Cys Val Thr Val Glu Asp Tyr Phe Asn Asp Phe
            580                 585                 590

Ala Lys Ile Lys Lys Pro Tyr Lys Lys Arg Met Thr Ala Glu Ala His
        595                 600                 605

Arg Arg Val Val Val Glu Tyr Leu Arg Ala Val Met Gln Lys Arg Ile
    610                 615                 620

Ser Phe Arg Ser Pro Glu Glu Arg Lys Glu Gly Ala Glu Lys Met Val
625                 630                 635                 640

Arg Glu Ala Glu Gln Leu Arg Phe Leu Phe Arg Lys Leu Ala Ser Gly
                645                 650                 655

Phe Gly Glu Asp Val Asp Gly Tyr Cys Asp Thr Ile Val Ala Val Ala
            660                 665                 670

Glu Val Ile Lys Leu Thr Asp Pro Ser Leu Leu Tyr Leu Glu Val Ser
        675                 680                 685

Thr Leu Val Ser Lys Tyr Pro Asp Ile Arg Asp Asp His Ile Gly Ala
    690                 695                 700

Leu Leu Ala Val Arg Gly Asp Ala Ser Arg Asp Met Lys Gln Thr Ile
705                 710                 715                 720

Met Glu Thr Leu Glu Gln Gly Pro Ala Gln Ala Ser Pro Ser Tyr Val
                725                 730                 735
```

-continued

```
Pro Leu Phe Lys Asp Ile Val Val Pro Ser Leu Asn Val Ala Lys Leu
            740                 745                 750

Leu Lys
```

(2) INFORMATION FOR SEQ ID NO:2:

(i) SEQUENCE CHARACTERISTICS:
(A) LENGTH: 2464 base pairs
(B) TYPE: nucleic acid
(C) STRANDEDNESS: single
(D) TOPOLOGY: linear (vii) IMMEDIATE SOURCE:
(A) LIBRARY: LEUKNOT02
(B) CLONE: 1874686

(xi) SEQUENCE DESCRIPTION: SEQ ID NO:2:

```
AGGAGGTGCA CAGAGAACAC CCCTAGCATG AACAGTGTGA GGATTCCACC AGCTTTTTCA     60

CCATGAAGGA GACAGACCGG GAGGCCGTTG CGACAGCAGT GCAAAGGGTT GCTGGGATGC    120

TCCAGCGCCC GGACCAGCTG GACAAGGTGG AGCAGTATCG CAGGAGAGAA GCGCGGAAGA    180

AGGCCTCCGT GGAGGCCAGA TTGAAGGCCG CCATCCAGTC ACAGTTGGAC GGGGTGCGCA    240

CAGGCCTCAG CCAGCTCCAC AACGCCCTGA ATGACGTCAA AGACATCCAG CAGTCGCTGG    300

CAGACGTCAG CAAGGACTGG AGGCAGAGCA TCAACACCAT TGAGAGCCTC AAGGACGTCA    360

AAGACGCCGT GGTGCAGCAC AGCCAGCTCG CCGCAGCCGT GGAGAACCTC AAGAACATCT    420

TCTCAGTGCC TGAGATTGTG AGGGAGACCC AGGACCTAAT TGAACAAGGG GCACTCCTGC    480

AAGCCCACCG GAAGCTGATG GACCTGGAGT GCTCCCGGGA CGGGCTGATG TACGAGCAGT    540

ACCGCATGGA CAGTGGGAAC ACGCGTGACA TGACCCTCAT CCATGGCTAC TTTGGCAGCA    600

CGCAGGGGCT CTCTGATGAG CTGGCTAAGC AGCTGTGGAT GGTGCTGCAG AGGTCACTGG    660

TCACTGTCCG CCGTGACCCC ACCTTGCTGG TCTCAGTTGT CAGGATCATT GAAAGGGAAG    720

AGAAAATTGA CAGGCGCATA CTTGACCGGA AAAAGCAAAC TGGCTTTGTT CCTCCTGGGA    780

GGCCCAAGAA TTGGAAGGAG AAAATGTTCA CCATCTTGGA GAGGACTGTG ACCACCAGAA    840

TTGAGGGCAC ACAGGCAGAT ACCAGAGAGT CTGACAAGAT GTGGCTTGTC CGCCACCTGG    900

AAATTATAAG GAAGTACGTC CTGGATGACC TCATTGTCGC CAAAAACCTG ATGGTTCAGT    960

GCTTTCCTCC CCACTATGAG ATCTTTAAGA ACCTCCTGAA CATGTACCAC CAAGCCCTGA   1020

GCACGCGGAT GCAGGACCTC GCATCGGAAG ACCTGGAAGC CAATGAGATC GTGAGCCTCT   1080

TGACGTGGGT CTTAAACACC TACACAAGTA CTGAGATGAT GAGGAACGTG GAGCTGGCCC   1140

CGGAAGTGGA TGTCGGCACC CTGGAGCCAT TGCTTTCTCC ACACGTGGTC TCTGAGCTGC   1200

TTGACACGTA CATGTCCACG CTCACTTCAA ACATCATCGC CTGGCTGCGG AAAGCGCTGG   1260

AGACAGACAA GAAAGACTGG GTCAAAGAGA CAGAGCCAGA AGCCGACCAG GACGGGTACT   1320

ACCAGACCAC ACTCCCTGCC ATTGTCTTCC AGATGTTTGA ACAGAATCTT CAAGTTGCTG   1380

CTCAGATAAG TGAAGATTTG AAAACAAAGG TACTAGTTTT ATGTCTTCAG CAGATGAATT   1440

CTTTCCTAAG CAGATATAAA GATGAAGCGC ACTGGTATAA AGAAGAGCAC CTGAGGAATC   1500

GGCAGCACCC TCACTGCTAC GTTCAGTACA TGATCGCCAT CATCAACAAC TGCCAGACCT   1560

TCAAGGAATC CATAGTCAGT TTAAAAAGAA AGTATTTAAA GAATGAAGTG GAAGAGGGTG   1620

TGTCTCCGAG CCAGCCCAGC ATGGACGGGA TTTTAGACGC CATCGCGAAG GAGGGCTGCA   1680

GCGGTTTGCT GGAGGAGGTC TTCCTGGACC TGGAGCAACA TCTGAATGAA TTGATGACGA   1740

AGAAGTGGCT ATTAGGGTCA AACGCTGTAG ACATTATCTG TGTCACCGTG GAAGACTATT   1800
```

-continued

```
TCAACGATTT TGCCAAAATT AAAAAGCCGT ATAAGAAGAG GATGACGGCC GAGGCGCACC  1860

GGCGCGTGGT GGTGGAGTAC CTGCGGGCGG TCATGCAGAA GCGCATTTCC TTCCGGAGCC  1920

CGGAGGAGCG CAAGGAGGGT GCCGAGAAGA TGGTTAGGGA GGCAGAGCAG CTGCGCTTCC  1980

TGTTCCGGAA GCTGGCGTCC GGTTTCGGGG AAGACGTGGA CGGATACTGC GACACCATCG  2040

TGGCTGTGGC CGAAGTGATC AAGCTGACAG ACCCTTCTCT GCTCTACCTG GAGGTCTCCA  2100

CTCTGGTCAG CAAGTATCCA GACATCAGGG ATGACCACAT CGGTGCGCTG CTGGCTGTGC  2160

GTGGGGACGC CAGCCGTGAC ATGAAGCAGA CCATCATGGA GACCCTGGAG CAGGGCCCAG  2220

CACAGGCCAG CCCCAGCTAC GTGCCCCTCT TCAAGGACAT TGTGGTGCCC AGCCTGAACG  2280

TGGCCAAGCT GCTCAAGTAG CCTCCGCCGG CCTGCCCTGC TCGCCCCTCC ACAGCCTCGG  2340

TCCCTGCCTT TAGAAACGCG GGACAGCTGA TTGCTCTCCT TGGCCACACG TGCTCCTTTT  2400

AGCTGCACGG CCTGTCTTTA GGTGCCAGTG TGATGCACCG GSTGTGGTCG AGTGAGCGTC  2460

CCGA                                                               2464
```

(2) INFORMATION FOR SEQ ID NO:3:

(i) SEQUENCE CHARACTERISTICS:
(A) LENGTH: 755 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 1163174

(xi) SEQUENCE DESCRIPTION: SEQ ID NO:3:

```
Met Cys Lys Asp Ser Ala Cys Phe Ser Thr Met Lys Glu Thr Asp Leu
 1               5                  10                  15

Glu Ala Val Ala Thr Ala Val Gln Arg Val Ala Gly Met Leu Gln Arg
            20                  25                  30

Pro Asp Gln Leu Asp Lys Val Glu Gln Tyr Arg Arg Arg Glu Ala Arg
        35                  40                  45

Lys Lys Ala Ser Val Glu Ala Arg Leu Lys Ala Ala Ile Gln Ser Gln
    50                  55                  60

Leu Asp Gly Val Arg Thr Gly Leu Ser Gln Leu His Asn Ala Leu Asn
65                  70                  75                  80

Asp Val Lys Asp Ile Gln Gln Ser Leu Ala Asp Val Ser Lys Asp Trp
                85                  90                  95

Arg Gln Ser Ile Asn Thr Ile Glu Ser Leu Lys Asp Val Lys Asp Ala
            100                 105                 110

Val Val Gln His Ser Gln Leu Ala Ala Ala Val Glu Asn Leu Lys Asn
        115                 120                 125

Ile Phe Ser Val Pro Glu Ile Val Arg Glu Thr Gln Asp Leu Ile Glu
    130                 135                 140

Gln Gly Ala Leu Leu Gln Ala His Arg Lys Leu Met Asp Leu Glu Cys
145                 150                 155                 160

Ser Arg Asp Gly Leu Met Cys Glu Gln Tyr Arg Met Asp Ser Gly Asn
                165                 170                 175

Lys Arg Asp Met Thr Leu Ile His Gly Tyr Phe Gly Ser Thr Gln Gly
            180                 185                 190

Leu Ser Asp Glu Leu Ala Lys Gln Leu Trp Met Val Leu Gln Arg Ser
        195                 200                 205

Leu Val Thr Val Arg Arg Asp Pro Thr Leu Leu Val Ser Val Val Arg
    210                 215                 220
```

```
Ile Ile Glu Arg Glu Glu Lys Ile Asp Arg Arg Ile Leu Asp Arg Lys
225                 230                 235                 240

Lys Gln Thr Gly Phe Val Pro Pro Gly Arg Pro Lys Asn Trp Lys Glu
                245                 250                 255

Lys Met Phe Ala Val Leu Asp Arg Thr Val Thr Thr Arg Ile Glu Gly
            260                 265                 270

Thr Gln Ala Asp Thr Arg Glu Ser Asp Lys Met Trp Leu Val Arg His
        275                 280                 285

Leu Glu Ile Ile Arg Lys Tyr Val Leu Asp Asp Leu Val Ile Ala Lys
    290                 295                 300

Asn Leu Leu Val Gln Cys Phe Pro Pro His Tyr Asp Ile Phe Lys Asn
305                 310                 315                 320

Leu Leu Ser Met Tyr His Gln Ala Leu Ser Ile Arg Met Gln Asp Leu
                325                 330                 335

Ala Ser Glu Asp Leu Glu Ala Asn Glu Ile Val Ser Leu Leu Thr Trp
            340                 345                 350

Val Leu Asn Thr Tyr Thr Ser Ala Glu Met Met Gly Asn Val Glu Leu
        355                 360                 365

Ala Pro Glu Val Asp Val Asn Ala Leu Glu Pro Leu Leu Ser Pro Asn
    370                 375                 380

Val Val Ser Glu Leu Leu Asp Thr Tyr Met Ser Thr Leu Thr Ser Asn
385                 390                 395                 400

Ile Ile Ala Trp Leu Arg Lys Ala Leu Glu Thr Asp Lys Lys Asp Trp
                405                 410                 415

Ser Lys Glu Thr Glu Pro Glu Ala Asp Gln Asp Gly Tyr Tyr Gln Thr
            420                 425                 430

Thr Leu Pro Ala Ile Val Phe Gln Met Phe Glu Gln Asn Leu Gln Val
        435                 440                 445

Ala Ala Gln Ile Ser Glu Asp Leu Lys Thr Lys Val Leu Val Leu Cys
    450                 455                 460

Leu Gln Gln Met Asn Ser Phe Leu Ser Arg Tyr Lys Glu Glu Ala Gln
465                 470                 475                 480

Leu Tyr Lys Glu Glu His Leu Arg Asn Arg Gln His Pro His Cys Tyr
                485                 490                 495

Val Gln Tyr Met Val Ala Ile Ile Asn Asn Cys Gln Thr Phe Lys Glu
            500                 505                 510

Ser Ile Ile Ser Leu Lys Arg Lys Tyr Leu Lys Pro Glu Thr Glu Glu
        515                 520                 525

Ser Leu Cys Gln Ser Gln Pro Ser Met Asp Gly Ile Leu Asp Ala Ile
    530                 535                 540

Ala Lys Glu Gly Cys Ser Ser Leu Leu Glu Glu Val Phe Leu Asp Leu
545                 550                 555                 560

Glu Gln His Leu Asn Glu Leu Met Thr Lys Lys Trp Met Leu Gly Ser
                565                 570                 575

Asn Ala Val Asp Ile Ile Cys Val Thr Val Glu Asp Tyr Phe Asn Asp
            580                 585                 590

Phe Ala Lys Ile Lys Lys Pro Tyr Lys Lys Arg Met Thr Ala Glu Ala
        595                 600                 605

His Arg Arg Val Val Val Glu Tyr Leu Arg Ala Val Met Gln Lys Arg
    610                 615                 620

Ile Ser Phe Arg Ser Ala Glu Glu Arg Lys Glu Gly Ala Glu Lys Met
625                 630                 635                 640

Val Arg Glu Ala Glu Gln Leu Arg Phe Leu Phe Arg Lys Leu Ala Ser
```

-continued

```
                645                 650                 655

Gly Phe Gly Glu Asp Ala Asp Gly His Cys Asp Thr Ile Val Ala Val
            660                 665                 670

Ala Glu Val Ile Lys Leu Thr Asp Pro Ser Leu Leu Tyr Leu Glu Val
        675                 680                 685

Ser Thr Leu Val Ser Lys Tyr Pro Asp Ile Arg Asp Asp His Ile Gly
    690                 695                 700

Ala Leu Leu Ala Leu Arg Gly Asp Ala Ser Arg Asp Met Lys Gln Thr
705                 710                 715                 720

Ile Met Glu Thr Leu Glu Gln Gly Pro Met Gln Ala Ser Pro Asn Tyr
                725                 730                 735

Val Pro Ile Phe Gln Glu Ile Val Val Pro Ser Leu Asn Val Ala Lys
            740                 745                 750

Leu Leu Lys
        755
```